United States Patent
Watanabe

(10) Patent No.: US 10,156,436 B2
(45) Date of Patent: Dec. 18, 2018

(54) ILLUMINATION APPARATUS AND MEASUREMENT APPARATUS

(71) Applicant: OLYMPUS CORPORATION, Hachioji-shi, Tokyo (JP)

(72) Inventor: Daichi Watanabe, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/813,815

(22) Filed: Nov. 15, 2017

(65) Prior Publication Data
US 2018/0073863 A1   Mar. 15, 2018

Related U.S. Application Data

(63) Continuation of application No. PCT/JP2015/002736, filed on May 29, 2015.

(51) Int. Cl.
| | |
|---|---|
| G01B 11/24 | (2006.01) |
| G01B 11/25 | (2006.01) |
| A61B 1/00 | (2006.01) |
| A61B 1/06 | (2006.01) |
| G01B 11/30 | (2006.01) |

(Continued)

(52) U.S. Cl.
CPC ............ *G01B 11/2441* (2013.01); *A61B 1/00* (2013.01); *A61B 1/06* (2013.01); *G01B 11/24* (2013.01);
(Continued)

(58) Field of Classification Search
CPC ..... G01B 11/2441; G01B 11/25; G01B 11/30; G01B 11/24; G02B 27/283; G02B 27/286;
(Continued)

(56) References Cited

U.S. PATENT DOCUMENTS

| | | |
|---|---|---|
| 5,434,669 A | 7/1995 | Tabata et al. |
| 8,107,083 B2 | 1/2012 | Bendall et al. |

(Continued)

FOREIGN PATENT DOCUMENTS

| | | |
|---|---|---|
| JP | 62009249 A | 1/1987 |
| JP | 05087543 A | 4/1993 |
| JP | 05211988 A | 8/1993 |

OTHER PUBLICATIONS

International Search Report (ISR) and Written Opinion dated Aug. 18, 2015 issued in International Application No. PCT/JP2015/002736.

*Primary Examiner* — Sang H Nguyen
(74) *Attorney, Agent, or Firm* — Holtz, Holtz & Volek PC

(57) ABSTRACT

An illumination apparatus includes a light source including a semiconductor laser that emits coherent light, a polarization splitter including rutile, a half-phase retardation film, and another rutile to split optical paths by the polarization direction of incident light, and a projection polarization switching mechanism including a half-wave plate unit, a quarter-wave plate unit, and a polarizing film to switch projected light emitted from the polarization splitter between polarization components of light transmitted over optical paths split by the polarization splitter and a polarization component of light transmitted over any one optical path. As a result, a compact illumination apparatus, and a measurement apparatus using the same, with a common light source and optical system for both observation light and measurement light can be provided.

8 Claims, 4 Drawing Sheets

(51) Int. Cl.
*G02B 23/24* (2006.01)
*G02B 27/28* (2006.01)

(52) U.S. Cl.
CPC .............. *G01B 11/25* (2013.01); *G01B 11/30* (2013.01); *G02B 23/2461* (2013.01); *G02B 27/283* (2013.01); *G02B 27/286* (2013.01); *G02B 23/2469* (2013.01)

(58) Field of Classification Search
CPC .............. G02B 23/2461; G02B 26/105; G02B 23/2469; A61B 1/06
See application file for complete search history.

(56) References Cited

U.S. PATENT DOCUMENTS

| | | | |
|---|---|---|---|
| 2007/0121106 A1* | 5/2007 | Shibata | G01N 21/8806 356/237.2 |
| 2007/0127036 A1* | 6/2007 | Liao | G01B 11/2441 356/512 |
| 2008/0225260 A1* | 9/2008 | Klaassen | G03F 7/701 355/71 |
| 2013/0169935 A1* | 7/2013 | Schuck | G02B 27/26 353/8 |
| 2013/0284929 A1* | 10/2013 | Ouchi | G02F 1/3511 250/339.01 |
| 2013/0301096 A1* | 11/2013 | Takahashi | G02B 26/105 359/204.3 |
| 2014/0055594 A1* | 2/2014 | Nomura | G02B 21/06 348/79 |
| 2015/0362714 A1* | 12/2015 | Iga | A61B 1/00172 359/372 |
| 2016/0004221 A1* | 1/2016 | Ayres | G03H 1/2645 359/22 |
| 2016/0381352 A1* | 12/2016 | Palmer | G02B 5/3083 349/8 |

* cited by examiner

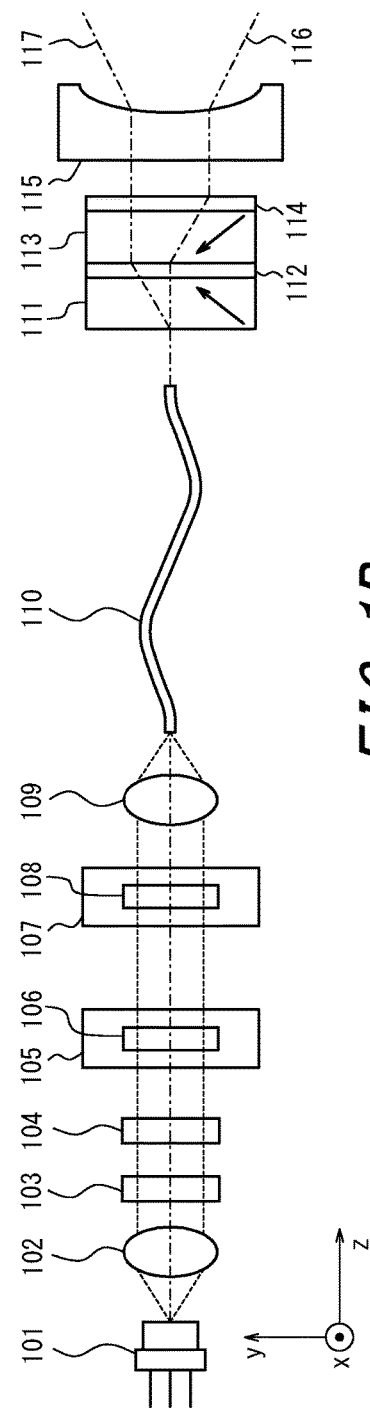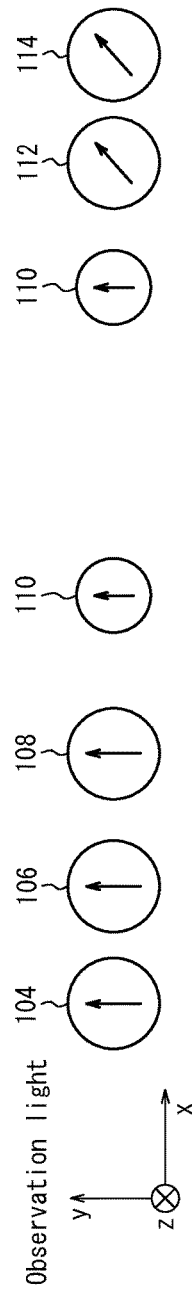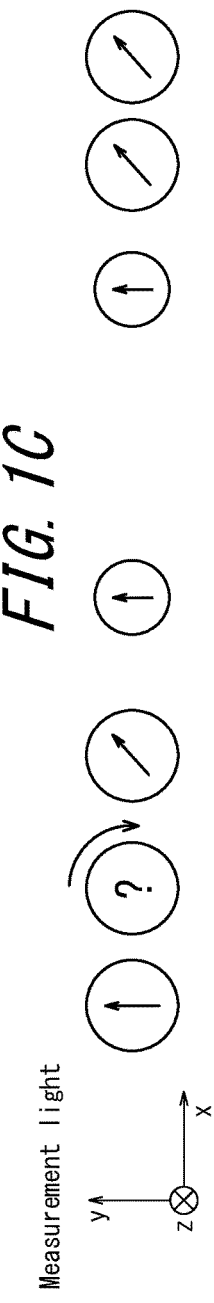

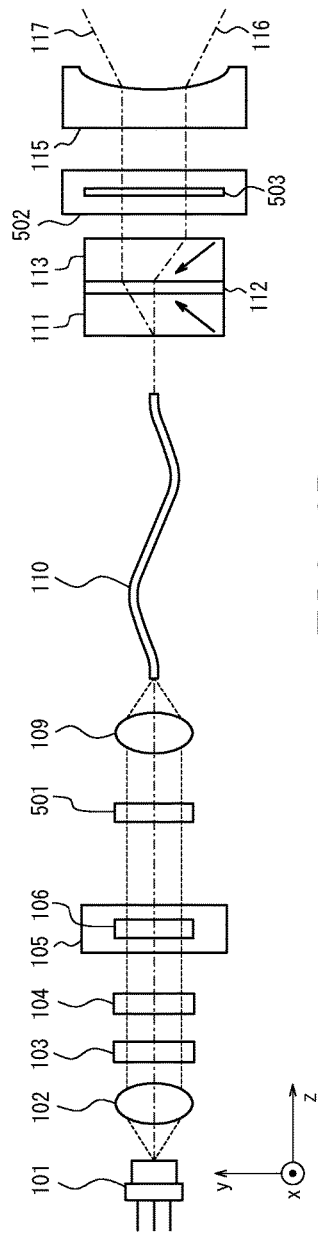
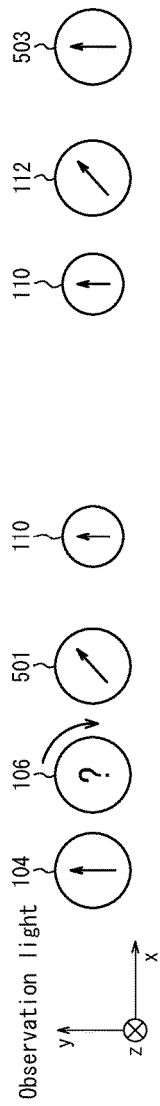
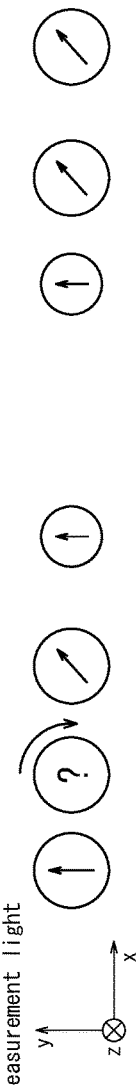
FIG. 6A
FIG. 6B
FIG. 6C

ILLUMINATION APPARATUS AND MEASUREMENT APPARATUS

CROSS-REFERENCE TO RELATED APPLICATION

The present application is a Continuing Application based on International Application PCT/JP2015/002736 filed on May 29, 2015, the entire disclosure of this earlier application being incorporated herein by reference.

TECHNICAL FIELD

The present disclosure relates to an illumination apparatus used in 3D shape measurement and to a measurement apparatus using the same.

BACKGROUND

Pattern projection is known as a non-contact method of measuring the 3D shape of an object surface (for example, patent literature (PTL) 1 and PTL 2). With this method, a specific standard pattern is first projected onto an object to be measured. The projected pattern, which deforms in accordance with the 3D shape of the surface on which the pattern is projected, is then captured with an imager from a different direction than the projection direction, and the imaged pattern is analyzed to calculate the 3D shape of the surface to be measured.

For example, PTL 1 discloses a measurement apparatus disposed at the tip of an endoscope. The phase shift method is used in this apparatus to measure the 3D shape of the surface of the object to be measured. With the phase shift method, an interference fringe is projected onto the object to be measured, the phase of a projected grid pattern is sequentially changed, and on the basis of captured image data, the initial phase distribution is calculated. The shape of the object surface can be calculated in accordance with this phase distribution by the principle of triangulation.

Such a measurement method based on pattern projection offers advantages such as not damaging the object for measurement by being a non-contact method, allowing measurement of soft objects, allowing rapid measurement and measurement of dynamically changing objects by virtue of instantaneously obtaining information over a wide range on the surface to be measured, and having a wider dynamic range of measurement than with interferometry. Hence, pattern projection is widely used in many fields.

CITATION LIST

Patent Literature

PTL 1: U.S. Pat. No. 8,107,083 B2
PTL 2: JP H5-211988 A

SUMMARY

An illumination apparatus according to one aspect of the present disclosure includes:
 a light source configured to emit coherent light;
 a polarization splitter configured to split an optical path of incident light by polarization direction; and
 a projection polarization switching mechanism configured to switch projected light emitted from the polarization splitter between polarization components of light transmitted over optical paths split by the polarization splitter and a polarization component of light transmitted over any one optical path.

According to one aspect, the projection polarization switching mechanism may include:
 a polarization adjuster disposed between the light source and the polarization splitter and configured to adjustably change a polarization state of the light emitted from the light source; and
 a polarizer disposed in a later stage than the polarization splitter and configured to transmit only linearly polarized light in a particular direction.

The polarization adjuster may include:
 a half-wave plate; and
 a half-wave plate rotator configured to adjust a direction of an optical axis of the half-wave plate by rotating the half-wave plate.

The polarization adjuster may further include:
 a quarter-wave plate on the polarization splitter side of the half-wave plate; and
 a quarter-wave plate rotator configured to adjust a direction of an optical axis of the quarter-wave plate by rotating the quarter-wave plate.

The polarization adjuster may include a phase adjuster disposed on the light source side of the half-wave plate and configured to control a phase difference between beams of polarized light whose optical paths are split by the polarization splitter.

According to another aspect, the projection polarization switching mechanism may include:
 a polarization adjuster disposed between the light source and the polarization splitter and configured to change a polarization state of the light emitted from the light source; and
 a polarizer disposed in a later stage than the polarization splitter and configured to adjust a direction of a transmission axis.

The polarization adjuster may include:
 a half-wave plate; and
 a half-wave plate rotator configured to adjust a direction of an optical axis of the half-wave plate by rotating the half-wave plate; and
 a quarter-wave plate on the polarization splitter side of the half-wave plate.

The illumination apparatus may further include a polarization-maintaining waveguide disposed between the light source and the polarization splitter so that polarization-maintaining directions of the polarization-maintaining waveguide are equivalent to polarization directions spilt by the polarization splitter.

A measurement apparatus according to one aspect of the present disclosure includes:
 one of the above illumination apparatuses;
 an imager configured to capture an image of an object, an interference fringe being projected on the object by the illumination apparatus; and
 a calculator configured to derive a shape of the object using the interference fringe in the image of the object captured by the imager and a positional relationship between the illumination apparatus and the imager.

BRIEF DESCRIPTION OF THE DRAWINGS

In the accompanying drawings:
 FIGS. 1A, 1B, and 1C illustrate the configuration of an illumination apparatus according to Embodiment 1, where FIG. 1A is a configuration diagram of an optical system, FIG. 1B illustrates the orientation of each optical element at the time of irradiation of observation light, and FIG. 1C illustrates the orientation of each optical element at the time of irradiation of measurement light;

FIGS. 6A, 6B, and 6C illustrate the configuration of an illumination apparatus according to Embodiment 5, where FIG. 6A is a configuration diagram of an optical system, FIG. 6B illustrates the orientation of each optical element at the time of irradiation of observation light, and FIG. 6C illustrates the orientation of each optical element at the time of irradiation of measurement light.

DETAILED DESCRIPTION

Figure 2:
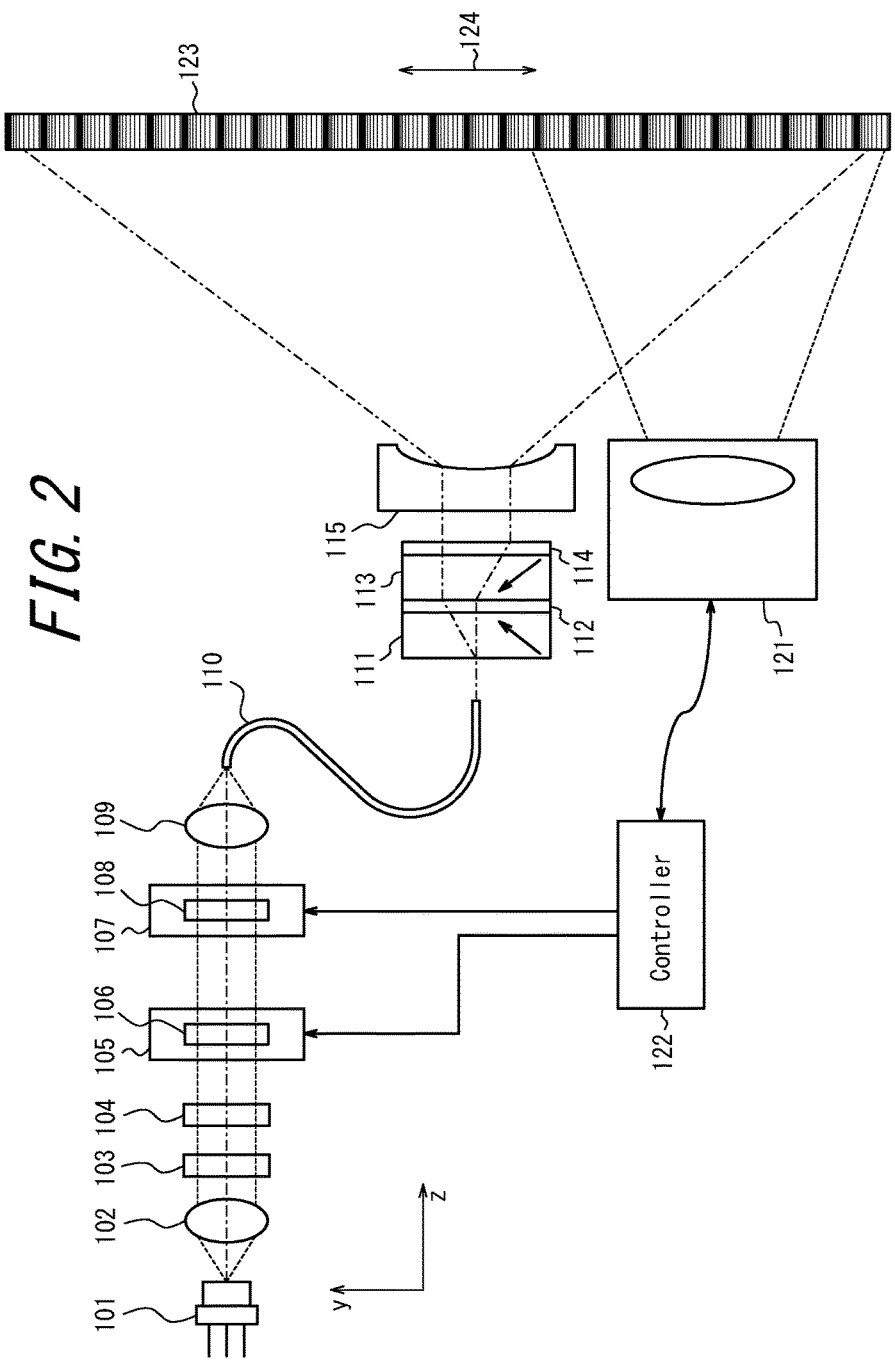
FIG. 2 illustrates the configuration of a measurement apparatus using the illumination apparatus according to Embodiment 1.

In a conventional measurement apparatus based on pattern projection, however, two illumination systems are provided: observation light for observing an object (no pattern) and measurement light for a measuring a 3D shape (pattern). Switching of the illumination is controlled by turning light sources on or off. Two light sources and optical systems are therefore necessary for the observation light and measurement light, increasing the size of the apparatus.

In light of these considerations, it would be helpful to provide a compact illumination apparatus in which a light source and optical system are shared between the observation light and measurement light and a measurement apparatus using this illumination apparatus.

Embodiments of this disclosure are described below with reference to the drawings.

Embodiment 1

FIGS. 1A, 1B, and 1C illustrate the configuration of an illumination apparatus according to Embodiment 1, where FIG. 1A is a configuration diagram of an optical system, FIG. 1B illustrates the orientation of each optical element at the time of irradiation of observation light, and FIG. 1C illustrates the orientation of each optical element at the time of irradiation of measurement light.

As illustrated in FIG. 1A, an illumination apparatus includes a semiconductor laser 101 as an illumination light source and includes, in the order of transmission of light emitted from the semiconductor laser 101, a collimator lens 102, a half-wave plate 103, a polarizing plate 104, a half-wave plate unit 105, a quarter-wave plate unit 107, a coupling lens 109, a polarization-maintaining and absorption-reducing (PANDA) fiber 110 (polarization-maintaining waveguide), rutile 111, a half-phase retardation film 112, rutile 113, a polarizing film 114 (polarizer), and a wide-angle projection lens 115.

The light source in this embodiment includes the semiconductor laser 101, collimator lens 102, half-wave plate 103, and polarizing plate 104, and the polarization splitter includes the rutile 111, half-phase retardation film 112, and rutile 113. The projection polarization switching mechanism includes the half-wave plate unit 105, quarter-wave plate unit 107, and polarizing film 114. Among these, the half-wave plate unit 105 and the quarter-wave plate unit 107 constitute the polarization adjuster.

In FIGS. 1A and 1B and the figures below, the direction along the principal light ray of light emitted from the semiconductor laser 101 is considered to be the z-direction, and the directions orthogonal to each other in a plane orthogonal to the z-direction are considered to be the x-direction and the y-direction.

The light emitted from the semiconductor laser 101 is formed as a parallel light beam by the collimator lens 102, passes through the half-wave plate 103, polarizing plate 104, half-wave plate unit 105, and quarter-wave plate unit 107, and is coupled to the PANDA fiber 110 through the coupling lens 109. The light coupled to the PANDA fiber 110 is guided through the PANDA fiber 110 and exits from a different end face than the entrance face. When the emitted light passes through the rutile 111, half-phase retardation film 112, and rutile 113, the optical paths are branched by the polarization direction. Each beam of the branched light passes through the polarizing film 114 to become linearly polarized light having a polarization component only in the transmission axis direction of the polarizing film 114. The light transmitted by the polarizing film 114 is formed into an illumination light beam by the wide-angle projection lens 115.

The wavelength of light emitted from the semiconductor laser 101 is, for example, 650 nm, and all of the optical elements are optimized to function for 650 nm light. Furthermore, an anti-reflection film is applied to the boundary surface of the members through which light passes. The semiconductor laser 101 may, of course, be a laser of a different wavelength, a variable wavelength laser, a light source unit that emits light of multiple wavelengths, or the like.

The polarizing plate 104 is arranged so that the transmission axis thereof is in the y-direction. Only linearly polarized light in the y-direction is transmitted by the polarizing plate 104. The half-wave plate 103 is disposed by adjusting the direction of the optical axis thereof to maximize the amount of light transmitted by the polarizing plate 104. The half-wave plate unit 105 includes a half-wave plate 106 and a non-illustrated rotation driving system (half-wave plate rotator). The quarter-wave plate unit 107 includes a quarter-wave plate 108 and a non-illustrated rotation driving system (quarter-wave plate rotator). The half-wave plate 106 and the quarter-wave plate 108 are adjusted to any rotation angle about the z-axis in accordance with a control signal from a non-illustrated controller unique to the illumination apparatus or the controller of the below-described measurement apparatus that uses the illumination apparatus.

The PANDA fiber 110 is a polarization-maintaining fiber that uses birefringence. In a polarization-maintaining fiber, the direction with a high refractive index and the direction with a low refractive index are respectively referred to as the slow axis and fast axis, and polarized waves are maintained with respect to these axes for guided light. In other words, when considering light incident on one end of the polarization-maintaining fiber as being divided into two linear polarization components in the slow axis direction and the fast axis direction, then light of the linear polarization component parallel to the slow axis is emitted from the other end of the polarization-maintaining fiber as linearly polarized light parallel to the slow axis, and light of the linear polarization component parallel to the fast axis is emitted from the other end of the polarization-maintaining fiber as linearly polarized light parallel to the fast axis. In this embodiment, the PANDA fiber 110 is arranged so that the slow axis thereof is in the y-direction. The following description, however, also holds when the slow axis is in the x-direction.

The rutiles 111 and 113 are uniaxial birefringent crystals and are, for example, flat plates each having a thickness of 0.35 mm. The angle between the optical axis and a normal to the surface of the flat plate can be set to 48°. This angle is a condition for maximizing the split width by which the rutile splits the polarized light. The condition for maximizing the split width of the birefringent crystal flat plate is that the angle between the optical axis and the normal to the surface of the flat plate be $\arctan(n_e/n_o)$, where $n_o$ and $n_e$ are the refractive indices of the birefringent crystal for ordinary light and extraordinary light, respectively.

The optical axes of the rutile 111 and the rutile 113 are arranged to be parallel to the y-z plane and not to be parallel to each other. In other words, the optical axes of the rutile 111 and the rutile 113 are inverted only in the z-direction. The half-phase retardation film 112 is disposed between the rutile 111 and the rutile 113 so that the optical axis thereof is at a 45° angle relative to the x-axis in the x-y plane. As a result, the polarization direction of a light beam 116 passing through the rutile 111 as ordinary light is rotated upon the light beam 116 passing through the half-phase retardation film 112. The light beam 116 then passes through the rutile 113 as extraordinary light. The polarization direction of a light beam 117 passing through the rutile 111 as extraordinary light is rotated upon the light beam 117 passing through the half-phase retardation film 112. The light beam 117 then passes through the rutile 113 as ordinary light.

At this time, upon looking at the optical emission point of the PANDA fiber 110 through the ruffle 113, half-phase retardation film 112, and rutile 111 from the emission side of the illumination light, two virtual images are observed at positions symmetrical with respect to the actual optical emission point of the PANDA fiber 110 in the x-y plane.

The polarizing film 114 is arranged so that the transmission axis thereof is at a 45° angle relative to the x-axis in the x-y plane. The light beams 116, 117 whose optical paths are branched by the rutile 111, half-phase retardation film 112, and rutile 113 are polarization components that are orthogonal to each other and do not form an interference fringe by virtue of not being coherent. However, the polarizing film 114 is used to extract only the polarization components that are coherent, thereby allowing interference fringes to be formed.

The wide-angle projection lens 115 is a concave lens and expands the diverging angle of the light beams emitted from the PANDA fiber 110. The wide-angle projection lens 115 may be a convex lens instead, in which case the light passing through the wide-angle projection lens 115 diverges after first converging.

Next, the switching between the observation light and measurement light by the projection polarization switching mechanism is described with reference to FIG. 1B and FIG. 1C. The transmission axis direction of the polarizing plate 104, the optical axis direction of the half-wave plate 106, the optical axis direction of the quarter-wave plate 108, the slow axis direction of the incident-side end face and the emission-side end face of the PANDA fiber 110, the optical axis direction of the half-phase retardation film 112, and the transmission axis direction of the polarizing film 114 are illustrated in FIGS. 1B and 1C respectively at the time of irradiation of observation light and the time of irradiation of measurement light. The optical axis directions of the half-wave plate 106 and the quarter-wave plate 108 differ between the time of irradiation of observation light and the time of irradiation of measurement light.

First, observation light is described. As illustrated in FIG. 1B, the half-wave plate 106 and the quarter-wave plate 108 are arranged so that the optical axes thereof are parallel to the y-direction. As a result, the light incident on the PANDA fiber 110 and the light emitted from the PANDA fiber 110 to the rutile 111 is only linearly polarized light parallel to the slow axis of the PANDA fiber 110. Since this linearly polarized light is only an ordinary light component with respect to the rutile 111 and is only an extraordinary light component with respect to the rutile 113, the optical path does not branch. In other words, light only travels the optical path of the light beam 116 in this case. Therefore, no interference fringe pattern appears in the projected light. If the rutile 111 and the rutile 113 are arranged in the opposite order, the ordinary light and extraordinary light are reversed, but in the same way as above, the optical path is not branched.

Next, measurement light is described. As illustrated in FIG. 1C, the quarter-wave plate 108 is arranged so that the optical axis thereof is at a 45° angle relative to the x-axis in the x-y plane. As a result, in the light that passes through the quarter-wave plate 108, the amplitude of the polarization components is equal in the x-axis direction and the y-axis direction. Furthermore, in the light incident on the PANDA fiber 110, the amplitude of the polarization components is equal in the slow axis direction and the fast axis direction, and the light incident on the rutile 111 also has two polarization components with equal amplitude in the x-axis direction and the y-axis direction. Therefore, the optical paths of the two polarization components are branched to the two light beams 116 and 117 in the rutile 111 and propagate through the rutile 111, the half-phase retardation film 112, and the rutile 113. Since the branched light beams 116 and 117 have equal amplitude, the light beams 116 and 117 that pass through the polarizing film 114 become two light beams with equal amplitude and polarization, forming an interference fringe with high contrast on an object.

Here, rotation of the optical axis of the half-wave plate 106 about the z-axis in the measurement light to allow scanning of the interference fringe projected on the object is described. In the light that passes through the half-wave plate 106 and the quarter-wave plate 108, a phase difference of δ rad occurs in the polarization component in the x-axis direction and the y-axis direction as compared to before the light passes through. This phase difference of δ rad relative to the rotation angle θ rad of the optical axis of the half-wave plate 106 is given by $\delta=\pi/2-4\theta$. In other words, by rotating the optical axis of the half-wave plate 106 with the z-axis as the axis of rotation, the phase difference of the polarization components in the slow axis direction and the fast axis direction of light incident on the PANDA fiber 110 can be changed. As a result, the phase difference of the light beams 116 and 117 branched by the rutile 111, half-phase retardation film 112, and rutile 113 can be changed. Since the brightness of the two-beam interference fringe changes sinusoidally with respect to the phase difference φ of the two light beams at any point, the brightness of any point on the object can be changed sinusoidally by rotating the optical axis of the half-wave plate 106 about the z-axis.

In this way, when the optical axis of the half-wave plate 106 is in the y-direction, the quarter-wave plate unit 107 has the function of switching the optical path of light passing through the polarization splitter by switching the direction of the optical axis between being in the y-direction and being at a 45' angle relative to the x-axis. When the optical axis of the quarter-wave plate 108 is at a 45° angle to the x-axis, the half-wave plate unit 105 controls the phase difference of polarized light traveling along the optical paths of the light beams 116 and 117.

Next, with reference to FIG. 2, a measurement apparatus is described. FIG. 2 illustrates the configuration of a measurement apparatus using the illumination apparatus according to Embodiment 1. The measurement apparatus includes the above-described illumination apparatus, a camera 121, and a controller 122. The camera 121 is placed at a distance from the wide-angle projection lens 115 in the scanning direction 124 of the interference fringe pattern 123. The camera 121 captures images in accordance with a control signal from the controller 122. The controller 122 is, for example, implemented by computer hardware provided with a CPU and a memory, is connected electrically to the half-wave plate unit 105 and quarter-wave plate unit 107, and controls the orientation of the optical axes of the half-wave plate 106 and quarter-wave plate 108. The user of the measurement apparatus can switch between observation light and measurement light using a non-illustrated input apparatus connected to the controller. The controller 122 also functions as a calculator that derives the shape of an object using the interference fringe in an image of the object captured by the camera 121 and the positional relationship between the wide-angle projection lens 115 of the illumination apparatus and the camera 121. The measurement apparatus is not limited to the illumination apparatus according to Embodiment 1 and may be configured similarly when using the illumination apparatus according to any of Embodiments 2 to 5 below.

As described above, according to this embodiment, the polarization state of light emitted from the same semiconductor laser 101 can be changed with the quarter-wave plate unit 107, and a polarization state having polarization components that are substantially equal in the x-direction and the y-direction can be switched with linearly polarized light having only a polarization component in the y-direction. As a result, the projected light can be switched between i) polarization components (measurement light) that are transmitted over both of the optical paths of the light beams 116 and 117 split by the rutile 111, half-phase retardation film 112, and rutile 113 and ii) a polarization component (observation light) that is transmitted over the optical path of one light beam 116. In other words, according to this embodiment, a common light source and optical system can be used for the measurement light and the observation light, allowing a reduction in size of the illumination apparatus and the measurement apparatus.

By providing the half-wave plate unit 105, the phase difference can be adjusted between the light beam 116 and the light beam 117 passing through the two optical paths that are branched in the measurement light. As a result, an interference fringe can be measured by illuminating an object using different phase differences. This approach is suitable for 3D shape measurement based on the phase shift method.

Furthermore, since the PANDA fiber 110 is provided between the coupling lens 109 and the rutile 111, the light emitted from the quarter-wave plate 108 (polarization adjuster) is incident on the rutile 111 (polarization splitter) in a state that maintains the polarization components in the fast axis and slow axis directions. As a result, when applying this disclosure to endoscopes or the like, the polarization components are maintained well even when the light is guided by the PANDA fiber 110 over a long distance, allowing good measurement when irradiating measurement light.

Embodiment 2

Figure 3:
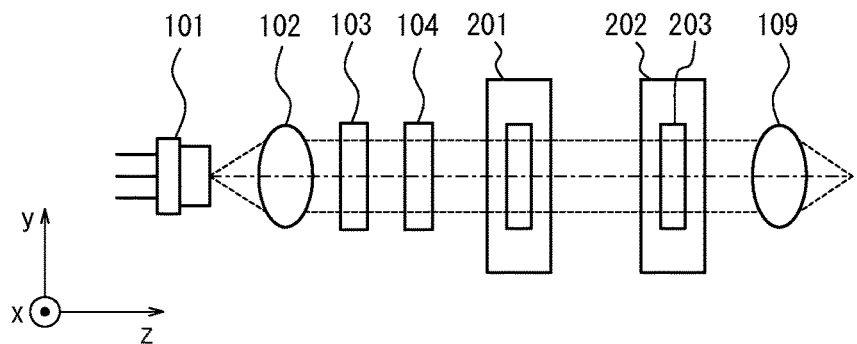
FIG. 3 illustrates the configuration of an illumination apparatus according to Embodiment 2.

FIG. 3 illustrates an illumination apparatus according to Embodiment 2. This illumination apparatus has the configuration of the illumination apparatus of Embodiment 1, without the half-wave plate unit 105 and the quarter-wave plate unit 107, and with the addition of a liquid crystal retarder 201 and a half-wave plate unit 202. Since the remaining configuration is similar to that of Embodiment 1, identical constituent elements are labeled with the same reference signs, and a description thereof is omitted. In FIG. 3, the configuration of the optical system in the stage subsequent to the PANDA fiber 110 in FIG. 1 is omitted.

In this embodiment, the projection polarization switching mechanism includes the liquid crystal retarder 201, half-wave plate unit 202, and polarizing film 114. Among these, the liquid crystal retarder 201 and the half-wave plate unit 202 constitute the polarization adjuster. The liquid crystal retarder 201 corresponds to the phase adjuster.

In accordance with the control signal from a non-illustrated controller, the liquid crystal retarder 201 provides a phase difference between the linearly polarized light at an angle of 45° to the x-axis and the linearly polarized light at an angle of −45° to the x-axis. The half-wave plate unit 202 includes a half-wave plate 203 and a non-illustrated rotation driving system (half-wave plate rotator), and in accordance with a control signal from the non-illustrated controller, rotates the optical axis of the half-wave plate 203 relative to the z-axis to any rotation angle relative to the y-axis.

At the time of irradiation of observation light, the measurement apparatus of this embodiment only causes linearly polarized light parallel to the slow axis of the PANDA fiber 110 to be incident on the PANDA fiber 110. For example, such linearly polarized light can be obtained by setting the optical axis of the half-wave plate 203 to 0° relative to the x-axis if the retardation amount of the liquid crystal retarder 201 is θ rad.

On the other hand, for the measurement light, the direction of the optical axis of the half-wave plate 203 is set to a direction at a 22.5° angle relative to the x-axis. As a result, the two linear polarization components provided with a phase difference by the liquid crystal retarder 201 become polarization components in the x-direction and the y-direction and are incident as linearly polarized light respectively parallel to the fast axis and the slow axis of the PANDA fiber 110. In other words, the amplitude of the two projected light beams is equal, and the phase difference thereof can be changed by the liquid crystal retarder 201.

As described above, the same effects as in Embodiment 1 can be achieved in this embodiment. Furthermore, since the liquid crystal retarder with no mechanical driver is used as the phase modulator in this embodiment, the phase modulator does not easily break down, and the phase can be switched at high speed. Accordingly, the measurement speed at the time of measurement can be improved. When the interference fringe pattern projected from the illumination apparatus does not need to be changed, the liquid crystal retarder 201 need not be provided, and observation light and measurement light can be switched between with only the half-wave plate unit 202. In this case, the polarization adjuster can be configured by the half-wave plate unit 202 alone.

Embodiment 3

Figure 4:
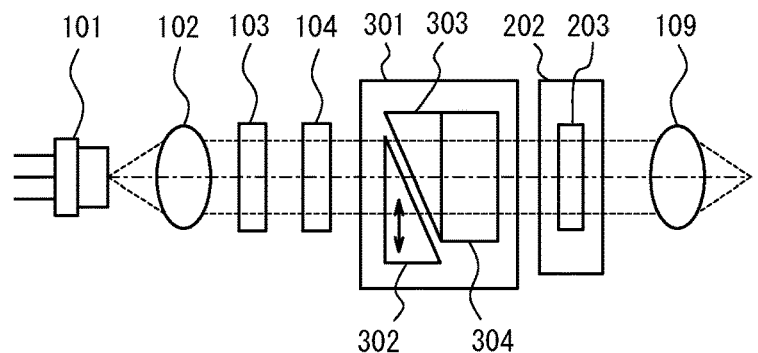
FIG. 4 illustrates the configuration of an illumination apparatus according to Embodiment 3.

FIG. 4 illustrates an illumination apparatus according to Embodiment 3. Instead of the liquid crystal retarder 201 of Embodiment 2, the illumination apparatus according to Embodiment 3 is provided with a Babinet-Soleil compensator 301 as the phase adjuster. Unlike FIG. 3, FIG. 4 is a view with the coordinate axes rotated by −45° about the z-axis. In other words, FIG. 4 is a view when the x-axis and y-axis are each tilted by 45°. In FIG. 4, as in FIG. 3, the configuration of the optical system in the stage subsequent to the PANDA fiber 110 is omitted.

The Babinet-Soleil compensator 301 includes liquid crystals 302, 303, and 304 and a non-illustrated linear drive system. The liquid crystals 302 and 303 have a shape that divides the flat plate of the left liquid crystal into two wedged prisms. The liquid crystal 304 is the right liquid crystal and has the same thickness as that of the flat plate yielded by combining the liquid crystal 302 and liquid crystal 303. The liquid crystal 302 is disposed in the non-illustrated linear drive system and is adjusted, in accordance with a control signal from a non-illustrated controller, to any position that is parallel to the x-y plane and at a 45° angle to the x-axis. The optical axes of the liquid crystals 302 and 303 are arranged in parallel to the x-y plane and at a 45° angle to the x-axis, and the optical axis of the liquid crystal 304 is arranged in parallel to the x-y plane and at a −45° angle to the x-axis. As a result, a phase difference can be provided between the linearly polarized light at an angle of 45° to the x-axis and the linearly polarized light at an angle of −45° to the x-axis by changing the position of the liquid crystal 302. Since the remaining configuration and operations are similar to those of Embodiment 2, identical constituent elements are labeled with the same reference signs, and a description thereof is omitted.

According to this embodiment, the same effects as in Embodiment 1 are obtained, and by using a Babinet-Soleil compensator, a phase difference can be provided over a wide range of wavelengths.

Embodiment 4

Figure 5:
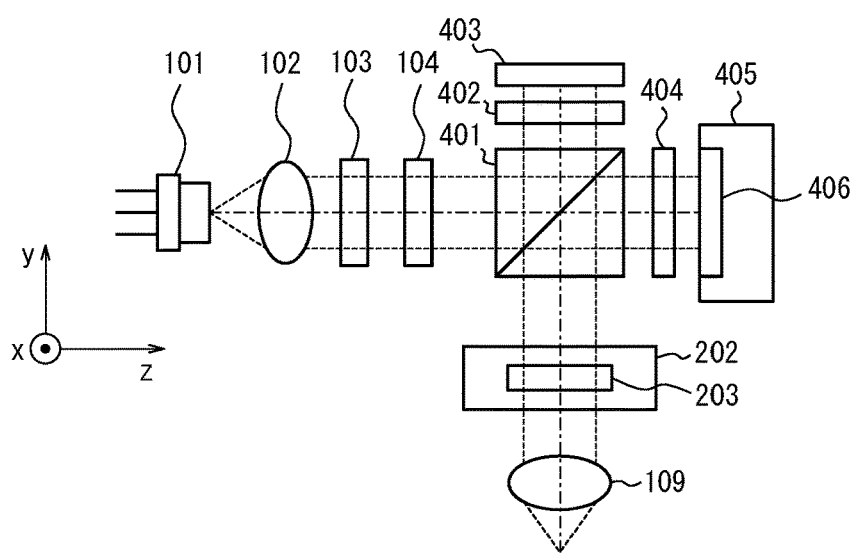
FIG. 5 illustrates the configuration of an illumination apparatus according to Embodiment 4.

FIG. 5 illustrates an illumination apparatus according to Embodiment 4. Instead of the liquid crystal retarder 201 of Embodiment 2, the illumination apparatus according to Embodiment 4 includes a polarization beam splitter 401, quarter-wave plates 402 and 404, a flat mirror 403, and a reflection-type phase modulator 405 as the phase adjuster. The direction of the transmission axis of the polarizing plate 104 also differs from Embodiment 2. Furthermore, the arrangement of the half-wave plate unit 202 differs from Embodiment 2.

The polarization beam splitter 401 is arranged so that the beam splitter surface is perpendicular to the y-z plane, and a normal thereto is at a 45° angle relative to the z-axis. The polarization beam splitter 401 reflects linearly polarized light parallel to the x-direction and transmits linearly polarized light parallel to the y-direction. The flat mirror 403 is arranged in the y-direction of the polarization beam splitter 401 so that the normal direction thereof is in the principal light ray direction of light reflected by the polarization beam splitter 401. The reflection-type phase modulator 405 is arranged in the z-direction of the polarization beam splitter 401 so that the normal direction thereof is in the principal light ray direction of light transmitted by the polarization beam splitter 401. The quarter-wave plate 402 is arranged between the polarization beam splitter 401 and the flat mirror 403 so that the optical axis thereof is parallel to the x-z plane and at a 45° angle to the z-axis. The quarter-wave plate 404 is arranged between the polarization beam splitter 401 and the reflection-type phase modulator 405 so that the optical axis thereof is parallel to the x-y plane and at a 45° angle to the y-axis.

On the other hand, the polarizing plate 104 is arranged so that the transmission axis is in the x-y plane and is at a 45° angle to the x-axis. The half-wave plate 103 is arranged by adjusting the direction of the optical axis thereof to maximize the amount of light transmitted by the polarizing plate 104. Furthermore, the half-wave plate unit 202 is arranged on the opposite side from the face of the polarization beam splitter 401 where the quarter-wave plate 402 and the flat mirror 403 are provided, i.e. is arranged in the −y direction. Since the remaining configuration is similar to that of Embodiment 2, identical constituent elements are labeled with the same reference signs, and a description thereof is omitted.

With the above configuration, light emitted from the semiconductor laser 101 passes through the collimator lens 102 and the half-wave plate 103, is then formed by the polarizing plate 104 as linearly polarized light with a polarization direction inclined at a 45° angle relative to the x-direction, and is incident on the polarization beam splitter 401. The linear polarization component parallel to the x-direction in the light incident on the polarization beam splitter 401 is reflected by the beam splitter surface of the polarization beam splitter 401, passes though the quarter-wave plate 402 to become circularly polarized light, and is reflected by the flat mirror 403. The reflected, circularly polarized light passes though the quarter-wave plate 402 to become linearly polarized light parallel to the y-direction, passes through the beam splitter surface of the polarization beam splitter 401, and is incident on the half-wave plate unit 202. On the other hand, the linear polarization component parallel to the y-direction passes through the beam splitter surface of the polarization beam splitter 401, passes through the quarter-wave plate 404 to become circularly polarized light, and is reflected by the reflection-type phase modulator 405. The reflected, circularly polarized light passes though the quarter-wave plate 404 to become linearly polarized light parallel to the x-direction, is reflected by the beam splitter surface of the polarization beam splitter 401, and is incident on the half-wave plate unit 202.

The reflection-type phase modulator 405 includes a flat mirror 406 and a non-illustrated linear drive system. The flat mirror 406 is disposed in the linear drive system. The linear drive system receives a control signal from a non-illustrated controller and adjusts the position of the flat mirror 406 in the z-direction. As a result, the optical path length of light incident on the half-wave plate unit 202 through the reflection-type phase modulator 405 can be adjusted. Accordingly, the phase difference between the linearly polarized light parallel to the x-direction and the linearly polarized light parallel to the y-direction can be adjusted.

According to this embodiment, the same effects as in Embodiment 1 can be achieved. Furthermore, if a MEMS mirror is used as the reflection-type phase modulator, the effect of more rapid modulation than with other systems can be obtained. Furthermore, this embodiment has the advantage of higher durability with respect to temperature than a liquid crystal retarder.

Embodiment 5

With reference to FIGS. 6A to 6C, an illumination apparatus according to Embodiment 5 is described. FIG. 6A illustrates the configuration of the optical system, FIG. 6B illustrates the orientation of each optical element at the time of observation light, and FIG. 6C illustrates the orientation of each optical element at the time of measurement light. FIGS. 6B and 6C indicate the entrance face and emission face of the polarizing plate 104, half-wave plate 106, quarter-wave plate 501, and PANDA fiber 110 and the orientation of the half-phase retardation film 112 and a polarizing plate 503 by the same method as in FIG. 1B and FIG. 1C.

The illumination apparatus according to Embodiment 5 has the configuration of the illumination apparatus according to Embodiment 1, with the omission of the quarter-wave plate unit 107 and the polarizing film 114 and the addition of a quarter-wave plate 501 and a polarizing plate unit 502. In this case, the projection polarization switching mechanism is configured by the half-wave plate unit 105, quarter-wave plate 501, and polarizing plate unit 502. The quarter-wave plate 501 is arranged so that the optical axis thereof is parallel to the x-y plane and at a 45° angle relative to the x-axis. The polarizing plate unit 502 includes a non-illustrated rotation driving system and the polarizing plate 503. The polarizing plate 503 is disposed in the rotation driving system, and the rotation angle of the transmission axis thereof is adjusted in accordance with a control signal from a non-illustrated controller. Since the remaining configuration is similar to that of Embodiment 1, identical constituent elements are labeled with the same reference signs, and a description thereof is omitted.

With the above configuration, the transmission axis of the polarizing plate 503 is arranged in the y-direction by the polarizing plate unit 502 when irradiating observation light. As a result, the projected illumination light is only the polarization component of the light beam 116, so that no interference fringe pattern appears on the object.

On the other hand, when irradiating measurement light, the transmission axis of the polarizing plate 503 is arranged at a 45° angle relative to the x-axis. As a result, the projected illumination light includes both the polarization component of the light beam 116 and the polarization component of the light beam 117, so that an interference fringe pattern appears on the object. As in Embodiment 1, by rotating the half-wave plate 106, the phase difference between the light beam 116 and the light beam 117 is controlled, and the brightness of any point on the object can be changed sinusoidally.

According to this embodiment, the same effects as in Embodiment 1 can be obtained, and observation light and measurement light can be switched between by operating the polarizing plate unit disposed on the object side.

This disclosure is not limited to the above embodiments, and a variety of changes and modifications may be made. For example, the orientation of the x-direction and the y-direction, the orientation of the slow axis and the fast axis of the PANDA fiber 110, the order of arrangement of the rutile 111 and 113, and the like above are only examples. For example, the orientation of the x-direction and the y-direction in the optical system overall, the orientation of the slow axis and the fast axis of the PANDA fiber 110, and the order of the rutile 111 and the rutile 113 may be switched or otherwise changed while still obtaining similar effects. Furthermore, the optical crystals used in the polarization splitter are not limited to rutile ($TiO_2$). For example, a birefringent crystal such as calcite ($CaCO_3$), yttrium/vanadate ($YVO_4$), or the like may also be used.

The invention claimed is:

1. An illumination apparatus comprising:
   a light source configured to emit coherent light linearly polarized in a first direction;
   a polarization adjuster configured to change a polarization state of the light emitted from the light source between a first polarization state in which light is composed of a component parallel to the first direction and a second polarization state in which the light includes a component inclined with respect to the first direction, and to emit the light;
   a polarization splitter configured to split, in light incident from the polarization adjuster, the component parallel to the first direction from a component perpendicular to the first direction, and to direct the component parallel to the first direction to a first optical path and direct the component perpendicular to the first direction to a second optical path; and
   a polarizer configured to receive light that has passed through the polarization splitter and transmit only light that is linearly polarized in a particular direction,
   wherein:
   the light that has passed through the polarizer is divergent light to be irradiated on an object;
   in a case in which light in the first polarization state is emitted from the polarization adjuster, a light beam having passed through the first optical path is irradiated on the object; and
   in a case in which light in the second polarization state is emitted from the polarization adjuster, a light beam having passed through the first optical path and a light beam having passed through the second optical path overlap on the object, and interference fringes are formed on the object.

2. The illumination apparatus of claim 1, wherein the polarization adjuster comprises:
   a half-wave plate; and
   a half-wave plate rotator configured to adjust a direction of an optical axis of the half-wave plate by rotating the half-wave plate.

3. The illumination apparatus of claim 2, wherein the polarization adjuster further comprises:
   a quarter-wave plate on a polarization splitter side of the half-wave plate; and
   a quarter-wave plate rotator configured to adjust a direction of an optical axis of the quarter-wave plate by rotating the quarter-wave plate.

4. The illumination apparatus of claim 2, wherein the polarization adjuster further comprises a phase adjuster disposed on a light source side of the half-wave plate and configured to control a phase difference between beams of polarized light whose optical paths are split by the polarization splitter.

5. The illumination apparatus of claim 1, further comprising a polarization-maintaining waveguide disposed between the light source and the polarization splitter so that polarization-maintaining directions of the polarization-maintaining waveguide are equivalent to polarization directions spilt by the polarization splitter.

6. A measurement apparatus comprising:
   the illumination apparatus of claim 1;
   an imager configured to capture an image of an object, an interference fringe being projected on the object by the illumination apparatus; and
   a calculator configured to derive a shape of the object using the interference fringe in the image of the object captured by the imager and a positional relationship between the illumination apparatus and the imager.

7. The illumination apparatus of claim 1, wherein the polarization splitter comprises:
   a first birefringent crystal plate made of an uniaxial birefringent crystal;

a second birefringent crystal plate made of an uniaxial birefringent crystal; and a half-phase retardation film disposed between the first birefringent crystal plate and the second birefringent crystal plate;

wherein the first birefringent crystal plate and the second birefringent crystal plate are arranged such that respective optical axes thereof are parallel to a plane including the first direction and an optical axis of the polarization adjuster, and are not parallel to each other.

8. An illumination apparatus comprising:

a light source configured to emit coherent light linearly polarized in a first direction;

a half-wave plate to which the light emitted from the light source is incident, a direction of an optical axis of the half-wave plate being adjustable by rotation of the half-wave plate;

a quarter-wave plate to which light transmitted from the half-wave plate is incident, an optical axis of the quarter-wave plate being inclined with respect to the first direction;

a polarization splitter configured to split, in light incident from the quarter-wave plate, a component parallel to the first direction from a component perpendicular to the first direction, and to direct the component parallel to the first direction to a first optical path and direct the component perpendicular to the first direction to a second optical path;

a polarizer configured to receive light that has passed through the polarization splitter, a transmission axis of the polarizer being adjustable between the first direction and a second direction inclined with respect to the first direction by rotation of the polarizer;

wherein:

the light that has passed through the polarizer is divergent light to be irradiated on an object;

in a case in which the transmission axis of the polarizer is in the first direction, a light beam having passed through the first optical path is irradiated on the object; and in a case in which the transmission axis of the polarizer is in the second direction, a light beam having passed through the first optical path and a light beam having passed through the second optical path overlap on the object, and interference fringes are formed on the object.

* * * * *